(12) United States Patent
Rüdenauer et al.

(10) Patent No.: US 10,053,410 B2
(45) Date of Patent: Aug. 21, 2018

(54) PROCESS FOR PREPARING A MACROCYCLIC DIKETONE

(71) Applicant: BASF SE, Ludwigshafen (DE)

(72) Inventors: Stefan Rüdenauer, Weinheim (DE); Miriam Bru Roig, Heidelberg (DE); Andreas Ernst, Worms (DE); Thomas Fenlon, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/575,169

(22) PCT Filed: May 19, 2016

(86) PCT No.: PCT/EP2016/061221
§ 371 (c)(1),
(2) Date: Nov. 17, 2017

(87) PCT Pub. No.: WO2016/184948
PCT Pub. Date: Nov. 24, 2016

(65) Prior Publication Data
US 2018/0141888 A1    May 24, 2018

(30) Foreign Application Priority Data

May 20, 2015    (EP) .................... 15168462

(51) Int. Cl.
*C07C 45/30* (2006.01)
*C07C 49/00* (2006.01)
*C07C 49/385* (2006.01)

(52) U.S. Cl.
CPC ............ *C07C 45/30* (2013.01); *C07C 49/385* (2013.01); *C07C 2601/18* (2017.05)

(58) Field of Classification Search
CPC .... C07C 45/30; C07C 49/385; C07C 45/2601
See application file for complete search history.

(56) References Cited

FOREIGN PATENT DOCUMENTS

| CH | 513791 A | 10/1971 |
| CH | 519454 A | 2/1972 |
| CN | 102786398 A | 11/2012 |
| DE | 3610718 A1 | 12/1986 |
| GB | 1205047 A | 9/1970 |
| GB | 2176475 A | 12/1986 |

OTHER PUBLICATIONS

Ayres, D., et al., "Oxidation of Aromatic Substrates Part VII[1]. The Selective Oxidation of Phenolic Alkenes with Ruthenium Tetroxide", Tetrahedron, vol. 42, No. 15, (1986), pp. 4259-4265.
International Preliminary Report on Patentability for PCT/EP2016/061221 dated Apr. 24, 2017.
International Search Report for PCT/EP2016/061221 dated Jun. 17, 2016.
Lee, D., et al., "The Oxidation of Methyl Cinnamate by Ruthenium Tetroxide", Journal of Organic Chemistry, vol. 41, No. 22, (1976), p. 3644.
Okumoto, H., et al., "Use of the Composite Material RuO2/BaTi4O9 as an Environmentally Benign Solid Catalyst for the Oxidative Cleavage of Olefins", Synlett 2007, No. 20, (Dec. 2007), pp. 3201-3205.
Sonawane, et al., "On the Construction of Bicyclo [m.3.0] Bridged Alkenes: Thermal Rearrangement of Spirocyclic Vinylcyclopropanes", Tetrahedron Letters, vol. 33, No. 12, (1992), pp. 1645-1646.

*Primary Examiner* — Sikarl A Witherspoon
(74) *Attorney, Agent, or Firm* — Drinker Biddle & Reath LLP

(57) ABSTRACT

The present invention relates to a process for preparing a macrocyclic diketone compound of the formula (I), which comprises the oxidation of a bicycloolefine compound of the formula (II) with an oxidizing agent, formulae (I) (II) where in formulae (I) and (II) A is $(CH_2)_n$ with n being an integer from 2 to 12, where two hydrogen atoms may be replaced by $C_1$-$C_4$-alkyl, in particular methyl, or two hydrogen atoms, which are bound to adjacent carbon atoms may be replaced by a fused 5- or 6-membered saturated carbocycle; B is $(CH_2)_m$ with m being 1 or 2, where 1 or 2 hydrogen atoms may be replaced by $C_1$-$C_4$-alkyl, in particular methyl.

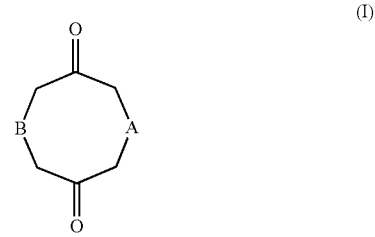

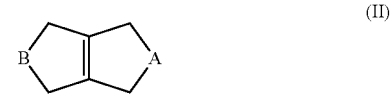

14 Claims, No Drawings

PROCESS FOR PREPARING A MACROCYCLIC DIKETONE

CROSS-REFERENCE TO RELATED APPLICATIONS

This application is a national stage application (under 35 U.S.C. § 371) of PCT/EP2016/061221, filed May 19, 2016, which claims benefit of European Application No. 15168462.8, filed May 20, 2015, both of which are incorporated herein by reference in their entirety.

The present invention relates to a process for preparing a macrocyclic diketone compound of the formula (I), which comprises the oxidation of a bicycloolefine compound of the formula (II) with an oxidizing agent,

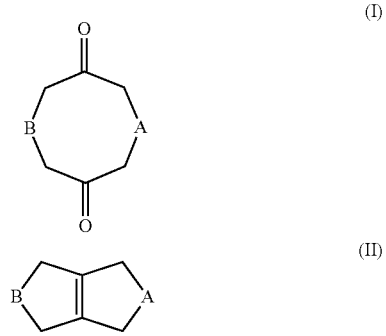

where in formulae (I) and (II)
A is $(CH_2)_n$ with n being an integer from 2 to 12, in particular 6 to 10, where two hydrogen atoms may be replaced by $C_1$-$C_4$-alkyl, in particular methyl, or two hydrogen atoms, which are bound to adjacent carbon atoms may be replaced by a fused 5- or 6-membered saturated carbocycle;
B is $(CH_2)_m$ with m being 1 or 2, where 1 or 2 hydrogen atoms may be replaced by $C_1$-$C_4$-alkyl, in particular methyl.

Macrocyclic diketons of the formula (I), in particular cyclopentadecane-1,5-dione or 3-methylcyclopentadecane-1,5-dione, which correspond to formula (I), where A is $CH_2$ or CH—$CH_3$ and B is $(CH_2)_8$, are interesting fragrances and may also serve as precursors for other macrocyclic musk odorants, such as muscone.

The preparation of macrocyclic diketones via oxidative cleavage of the double bond of bicycloolefine compounds is known in the art.

CH 519454 describes the preparation of cyclopentadecane-1,5-dione by ozonolysis of bicyclo[10.3.0]pentadecen [1(12)] or photooxidation of bicyclo[10.3.0]pentadecen[1(12)] with singlet oxygen, followed by acidic rearrangement of the resulting hydroperoxides. CH 519454 also describes the reaction of bicyclo[10.3.0]pentadecen[1(12)] with potassium permanganate. Ozonolysis and photooxidation are difficult to handle on large scale, while the use of potassium permanganate is comparatively expensive and requires a difficult and laborious work-up procedure.

CH 513791 describes a process for the preparation of cyclopentadecane-1,5-dione and 3-methylcyclopentadecane-1,5-dione, comprising the oxidation of bicyclo[10.3.0] pentadecen[1(12)] or 14-methylbicyclo[10.3.0]pentadecen [1(12)] with a sub-stoichiometric amount of 55% aqueous $H_2O_2$ in concentrated formic acid followed by reacting the intermediates with potassium hydroxide to yield bicyclo [10.3.0]pentadecan-1,12-diol or 14-methylbicyclo[10.3.0] pentadecan-1,12-diol, which is then cleaved by treatment with $Pb_3O_4$ in glacial acetic acid. The process is tedious and includes the use of toxic chemicals.

CN 102786398A describes the multi-step synthesis of 3-methylcyclopentadecane-1,5-dione starting from cyclododecanone, wherein the last step of the synthesis comprises the oxidation of 14-methylbicyclo[10.3.0]pentadecen[1(12)] with stoichiometric amounts of sodium periodate in the presence of the phase transfer catalyst tetrabutylammonium bromide to yield 3-methylcyclopentadecane-1,5-dione. Sodium periodate, which has to be applied in a more than four fold excess, is expensive and not easy to handle on industrial scales due to the high technical safety-requirements. Furthermore, the sodium periodate-waste has to be disposed. Due to these requirements and economical aspects, this process is inapplicable to industrial scale production.

The oxidation of substituted olefins with ruthenium compounds is generally known in the art.

Lee et al., J. Org. Chem., 1976, Vol. 41 (22), pp. 3644-3644, for example, describe the oxidation of methyl cinnamate compounds with stoichiometric amounts of ruthenium tetroxide.

Ayres et al., Tetrahedron, Vol. 42, No. 15, pp. 4259-4265, describe the selective oxidation of phenolic alkenes with ruthenium tetroxide. Specifically, the oxidation of trifluoroacetylated isoeugenol, trifluoroacetylated 4,4'-dihydroxy-α, β-dimethylstilbene and a rearrangement product of trifluoroacetylated norpregnenol with stoichiometric amounts of ruthenium tetroxide using carbon tetrachloride as solvent is described.

DE 3610718 describes a process for the production of glutaric acid, comprising the oxidation of cyclopentene using catalytic amounts of a ruthenium compound as oxidizing agent and stoichiometric amounts of a co-oxidizing agent, such as sodium hypochlorite. The oxidizing agent as well as the co-oxidizing agent is added in the form of an aqueous alkaline solution. The reaction is performed in a biphasic solvent system consisting of water and a chlorinated organic solvent.

To date, all reported processes for the oxidation of 14-methylbicyclo[10.3.0]pentadecen[1(12)] or bicyclo [10.3.0]pentadecen[1(12)] have major disadvantages when they are applied to industrial scale production.

Therefore, it is an object of the present invention to provide a process for efficiently producing the compound of formula (I), in particular cyclopentadecane-1,5-dione and 3-methylcyclopentadecane-1,5-dione. The process should be easy to handle and should allow the production of the compounds of formula (I) in good yields on industrial scales. Moreover, the use of toxic or expensive reagents should be avoided.

It was surprisingly found that the compounds of formula (II), in particular the compounds of formula (IIa), can be efficiently converted into the diketone compounds of formula (I), in particular into compounds of formula (Ia), if the oxidation of (II) or (IIa), respectively, is performed by using an oxidizing agent which comprises a catalytic amount of a ruthenium compound and a co-oxidizing agent selected from a non-transition metal containing oxidant.

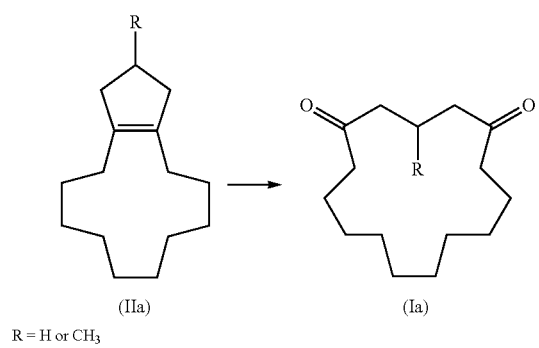

(IIa)    (Ia)

R = H or CH₃

Therefore, the present invention relates to a process for producing a diketone compound of formula (I) as described herein, which comprises the oxidation of the bicycloolefine compound of formula (II) with an oxidizing agent, where the oxidizing agent comprises a catalytic amount of a ruthenium compound and a co-oxidizing agent selected from a non-transition metal containing oxidant.

The present invention relates in particular to a process for producing 3-methylcyclopentadecane-1,5-dione of formula (Ia, R=CH₃) from 14-methylbicyclo[10.3.0]pentadecen[1(12)] of formula (IIa, R=CH₃), by the process as described herein.

The present invention also relates in particular to a process for producing cyclopentadecane-1,5-dione of formula (Ia, R=H) from bicyclo[10.3.0]pentadecen[1(12)] of formula (IIa, R=H), by the process as described herein.

The process according to the invention has several advantages over the prior art. The oxidation of the compounds of formula (II), in particular of the compounds of formula (IIa), by using a catalytic amount of a ruthenium compound as the oxidizing agent together with a co-oxidizing agent selected from a non-transition metal containing oxidant by the process as described herein, directly results in the formation of the compounds of formulae (I) or (Ia), respectively, with good yields and selectivity. In contrast to the processes described in the art, e.g. in CH 513791, CH 519454 and CN 102786398A, the present process can be easily performed on large scale, as the ruthenium compound as well as the co-oxidant are selected from nonhazardous compounds, and are, thus, much easier to handle than ozone, singlet oxygen, $Pb_3O_4$ or sodium periodate. Moreover, the use of expensive oxidants can be avoided and the ruthenium compound can be recycled for further use. As the reaction proceeds smoothly and with high selectivity, tedious work-up and large waste streams can be avoided.

For the purpose of the present invention, the expression "ruthenates" relates to any ruthenium salt containing the oxyanion $RuO_4^{2-}$.

For the purpose of the present invention, the expression "perruthenates" relates to any ruthenium salt containing the oxyanion $RuO_4^-$.

According to the process of the present invention, the total amount of ruthenium compound in the reaction mixture, calculated based on the number of ruthenium atoms, is typically in the range of from 0.001 to 0.2 mol, preferably in the range of from 0.005 to 0.15 mol, in particular in the range of from 0.01 to 0.1 mol, per 1 mol of compound of formula (II).

Generally, any ruthenium compound in the form of an inorganic ruthenium salt or an organic complex salt can be used as oxidizing agent in the process of the present invention. Suitable ruthenium compounds are for example ruthenium oxides, such as ruthenium(IV)oxide or ruthenium(VIII)oxide;

ruthenates, i.e. any ruthenium salt containing the oxyanion $RuO_4^{2-}$, e.g. the alkali or earth alkali metal salts thereof, such as magnesium-, strontium-, calcium-, barium- or sodium ruthenate;

perruthenates, i.e. any ruthenium salt containing the oxyanion $RuO_4^-$, e.g. the alkali or earth alkali metal salts thereof, such as sodium- or potassium perruthenates;

ruthenium halides, such as ruthenium(II) chloride, ruthenium(III) chloride, ruthenium(IV) chloride, ruthenium (III) bromide or ruthenium(III) iodide;

ruthenium nitrates, such as ruthenium(III) nitrate;

ruthenium(III) hydroxide;

ruthenium(IV) sulfate;

ruthenium carboxylates, such as ruthenium(III) acetate;

ruthenium complexes, such as ammonium hexachlororuthenate(IV), potassium hexachlororuthenate(IV), ammonium pentachloroaquaruthenate(III), potassium pentachloroaquaruthenate(III), hexaammine ruthenium (III) chloride, hexaammine ruthenium(III) bromide, hexaammine ruthenium(III) iodide, nitrosylpentaammine ruthenium(III) chloride, ruthenium(IV) ethylenediaminetetraacetate or ruthenium(0) dodecacarbonyl.

The above ruthenium compounds may be anhydrous or hydrated. The ruthenium compound may be used alone or in combination of two or more.

Preferably, the ruthenium compound used in the process of the invention is selected from ruthenium oxides, ruthenates, perruthenates, ruthenium halides, ruthenium nitrates and mixtures thereof.

Preferred ruthenium oxides are for example ruthenium tetroxide or ruthenium dioxide. Preferred ruthenates are for example magnesium ruthenate, calcium ruthenate or sodium ruthenate.

A preferred perruthenate is for example sodium perruthenate.

Preferred ruthenium halides are for example ruthenium (III) chloride, ruthenium(IV) chloride or ruthenium(III) bromide.

A preferred ruthenium nitrate is for example ruthenium (III) nitrate.

More preferably, the ruthenium compound used in the process of the present invention is selected from ruthenium tetroxide, sodium ruthenate, sodium perruthenate, ruthenium dioxide, ruthenium trichloride or mixtures thereof.

In particular, the ruthenium compound used in the process of the invention is ruthenium trichloride.

According to the process of the invention, the total amount of co-oxidizing agent used in the oxidation is typically in the range of from 2 to 10 mol, in particular in the range of from 3 to 8 mol, per 1 mol of compound of formula (II), whereby the molar amount of the oxidizing-agent specified above is calculated as oxygen equivalents.

For the purposes of the present invention, the term "oxygen equivalent" relates to the number of oxygen atoms that can be released by a given oxidant. For example, inorganic or organic peroxy acids as well as $H_2O_2$ can release one oxygen atom. Hypochlorite ($ClO^-$) can also release one oxygen atom, while chlorite ($ClO_2^-$) can typically release two oxygen atoms.

According to the invention, the co-oxidizing agent is selected from non-transition metal containing oxidants. A non-transition metal containing oxidant is an oxidant, which does not contain a transition metal. In principal, any non-transition metal containing oxidant that is capable of oxidizing a ruthenium compound having a low oxidation number to generate a ruthenium compound that is able to oxidize olefins can be used as co-oxidizing agent in the process of the present invention.

Suitable co-oxidizing agents that can be used in the process of the present invention are for example selected from halogens, oxygen, nitrous oxide, oxyanions of chlorine, dialkyl peroxides, organic peroxy acids, inorganic peroxy acids, peresters, i.e. esters of organic peroxy acids, hydroperoxides, hydrogen peroxide inorganic oxoacids, which do not contain a transition metal (i.e. non-transition metal containing inorganic oxoacids), and nitrate salts.

Suitable halogens are by way of example fluorine or chlorine.

Suitable oxyanions of chlorine are by way of example hypochlorites, chlorites, chlorates or perchlorates.

Suitable dialkyl peroxides are in particular di-$C_2$-$C_6$-alkyl peroxides are such as diisopropyl peroxide or di(tert.-butyl) peroxide.

Suitable organic peroxy acids include optionally halogen substituted peroxybenzoic acids, such as meta-chloroperoxybenzoic acid and $C_1$-$C_4$-alkanoic peracids, such as peracetic acid, perpropionic acid and perpivalic acid;

Suitable organic or inorganic include e.g. peroxydisulfuric acid and peroxymonosulphuric acid.

Peresters are esters of organic peroxy acids in particular alkyl esters of $C_1$-$C_4$-alkanoic peracids and aryl esters of $C_1$-$C_4$-alkanoic peracids, in particular alkyl esters and aryl esters of peracetic acid (peracetates) of perpropionic acid (perpropionates) or of perpivalic acid (perpivalates). In this context, the term "alkyl" relates to a saturated acyclic hydrocarbon radical having in particular 1 to 6 carbon atoms ($C_1$-$C_6$-alkyl). In this context, the term "aryl" relates to a phenyl or naphthyl, which are unsubstituted or substituted by 1, 2 or 3 radicals selected from fluorine, chlorine and $C_1$-$C_4$-alkyl. Suitable peresters are by way of example in particular peracetates, such as tert.-butyl peracetate or tert.-butyl phenylperacetate.

Hydroperoxides are in particular $C_1$-$C_6$-alkyl hydroperoxides. A suitable hydroperoxide is by way of example a tert.-butyl hydroperoxide.

Suitable non-transition metal containing inorganic oxoacids are for example sulphuric acid or nitric acid.

Suitable nitrate salts are for example sodium nitrate or potassium nitrate.

For the purpose of the present invention, the expressions "hypochlorites", "chlorites", "chlorates" or "perchlorates" relate to any salt containing the oxyanion $ClO^-$ (hypochlorite), $ClO_2^-$ (chlorite), $ClO_3^-$ (chlorate) or $ClO_4^-$ (perchlorate), respectively, e.g. the alkali or earth alkali metal salts thereof.

In particular, the co-oxidizing agent is selected from oxyanions of chlorine, dialkyl peroxides, hydrogen peroxide, organic and inorganic peroxy acids, nitrate salts, as well as mixtures thereof.

More preferably, the co-oxidizing agent is selected from oxyanions of chlorine, hydrogen peroxide, nitrate salts, as well as mixtures thereof.

Even more preferably, the co-oxidizing agent is selected from hypochlorites, e.g. lithium hypochlorite, sodium hypochlorite, potassium hypochlorite, magnesium hypochlorite, calcium hypochlorite, or barium hypochlorite; in particular it is sodium hypochlorite.

Generally, at least a part of the ruthenium compound, preferably the total amount of the ruthenium compound, is added to the compound of formulae (II) or (IIa) at the start of the reaction.

The co-oxidizing agent can be added at the start of the oxidation reaction or over the course of the oxidation reaction. The expression "course of the reaction" relates to the time interval between the start of the oxidation reaction, i.e. when the ruthenium compound and the compound of formula (II) or (IIa) are brought together and the reaction parameters are such that the oxidation reaction can take place, and the end of the reaction, i.e. when the compound of formula (II) or (IIa) is consumed and/or no further compound (I) or (Ia) is formed. It is preferred that the co-oxidizing agent is added over the course of the reaction. Thereby it is achieved that a steady amount of co-oxidizing agent is present in the reaction mixture. Adding the co-oxidizing agent over the course of the reaction is beneficial with regard to clean and rapid conversion.

The co-oxidizing agent can be added to the mixture of the compound of formulae (II) or (IIa) in one or more portions or continuously with constant or changing addition rates. Preferably, the co-oxidizing agent is added in several portions, e.g. in 3 to 20 portions, or continuously, preferably with constant addition rates, to the mixture of the compound of formulae (II) or (IIa).

It has been found beneficial, if the co-oxidizing agent is added in several portions, e.g. in defined amounts in regular time intervals, for example every 10 to 90 minutes, e.g. every 30 or 60 minutes, or continuously with constant addition rates to the mixture of the compound of formulae (II) or (IIa) over the whole course of the oxidation reaction.

Typically, the reaction time is in the range of from 1 to 16 hours, often in the range of from 1.5 to 12 hours.

In a preferred embodiment of the present invention, the co-oxidizing agent is added to the reaction mixture in the form of an alkaline aqueous solution, having a pH of at least pH 10, preferably of at least pH 12, for example pH 13 or pH 14.

In this preferred embodiment, the concentration of the co-oxidizing agent in the alkaline aqueous solution is in the range of from 1 to 50% by weight, preferably in the range of from 3 to 30% by weight, in particular in the range of from 5 to 20% by weight.

The alkaline aqueous solution is for example conveniently prepared by adding a strong mineral base, e.g. NaOH, KOH, or LiOH, in the form of a solid or an aqueous solution to an aqueous solution of the co-oxidizing agent. Generally the final concentration of the mineral base in the alkaline aqueous solution of the co-oxidizing agent is in the range of from 0.01 to 10 molar, preferably in the range of from 0.05 to 5 molar, in particular in the range of from 0.1 to 2 molar.

Generally, the molar ratio of the co-oxidizing agent to the ruthenium compound, which are applied to the reaction mixture, is in the range from 10:1 to 10000:1, preferably in the range of from 1:1 to 5000:1, in particular in the range of from 1:5 to 1000:1.

In a particular embodiment of the present invention, the oxidation of the compound of formulae (II) or (IIa) to give the compound of formulae (I) or (Ia) is conducted in such a way, that the pH of the reaction mixture is maintained in the range of from 7 to 14, preferably in the range of from 7 to 12, particularly in the range of from 7.5 to 11, and especially in the range of from 8.0 to 10.9.

The pH values given above relate to the pH of the aqueous phase of the reaction mixture, which results from the addition of the alkaline aqueous solution of the co-oxidizing agent to the reaction mixture comprising a water immiscible organic solvent, measured at 25° C.

The maintenance of the pH of the reaction mixture can be achieved by varying the pH of the alkaline aqueous solution of the co-oxidizing agent, e.g. by varying the concentration of the added mineral base, by adapting the addition rate of the alkaline aqueous solution of the co-oxidizing agent to the reaction mixture and/or by adding an aqueous buffer solution, comprising at least one buffering agent having a pKa-value in the range of from 8 to 12, to the reaction mixture.

It is preferred that the maintenance of the pH of the reaction mixture is either achieved by varying the pH of the alkaline aqueous solution of the co-oxidizing agent, e.g. by varying the concentration of the added mineral base, by adapting the addition rate of the alkaline aqueous solution of the co-oxidizing agent to the reaction mixture or by adding an aqueous buffer solution, comprising at least one buffering agent having a pKa-value in the range of from 8 to 12, to the reaction mixture.

In principal, any compound having a pKa-value in the range of from 8 to 12 is suitable as buffering agent. Suitable buffering agents having a pKa-value in the range of from 8 to 12, are for example selected from sodium hydrogen carbonate, potassium hydrogen carbonate, lithium carbonate, sodium carbonate, potassium carbonate, ammonium chloride, boric acid, sodium hydrogen borate, potassium hydrogen borate and mixtures thereof. Preferably, the buffering agent is selected from sodium hydrogen carbonate, potassium hydrogen carbonate, sodium carbonate, potassium carbonate, ammonium chloride ammonium, and mixtures thereof. In particular, the buffering agent is selected from a mixture of sodium hydrogen carbonate with sodium carbonate or potassium hydrogen carbonate with potassium carbonate.

Generally, the concentration of the at least one buffering agent in the aqueous buffer solution is in the range of from 0.01 to 5 molar, preferably in the range of from 0.1 to 2 molar.

Typically, the amount of the aqueous buffer solution that is added to the reaction mixture highly depends on the total concentration of the buffering agent in the aqueous buffer solution. Preferably, the amount of the aqueous buffer solution that is added to the reaction mixture is chosen such that the pH of the reaction mixture does not vary more than 4 pH units, preferably not more than 3 pH units, in particular not more than 2 pH units, over the whole course of the reaction.

Generally, the pH of the buffering solution is in the range of from 7 to 11, preferably in the range of from 8 to 10.

The aqueous buffer solution can be added to the mixture of the compound of formulae (II) or (IIa) in one or more portions or continuously with constant or changing addition rates. Preferably, the co-oxidizing agent is added in one portion to the mixture of the compound of formulae (II) or (IIa) at the start of the oxidation reaction.

The reaction can be principally performed in accordance with standard procedures of organic chemistry.

The temperature which is required to achieve the oxidation of the compound of formulae (II) or (IIa) to the compound of formulae (I) or (Ia) may vary. Frequently, the oxidation of the compound of formulae (II) or (IIa) to the compound of formulae (I) or (Ia), respectively, is performed at a temperature in the range of from −20 to 100° C., in particular from 0 to 80° C. and especially from 10 to 40° C.

The reaction pressure is of minor importance. In particular, the reaction is performed in a non-pressured vessel having pressurized balance with the ambient air.

The oxidation reaction can take place in the absence of or in the presence of an inert gas. The expression inert gas generally means a gas which under the prevailing reaction conditions does not enter into any reactions with the starting materials, reagents, or solvents participating in the reaction, nor with the resultant products. Examples of inert gases are $N_2$, $CO_2$ and noble gases like He, Ne, Ar, Kr and Xe. If the oxidation reaction is performed in the presence of an inert gas, the inert gas is preferably selected from $N_2$ or Ar.

The oxidation of the compounds of formulae (II) or (IIa) to give the compounds of formulae (I) or (Ia) can be carried out in bulk, i.e. in the absence of any added solvent or in the presence of one or more organic solvents.

It is preferred that the oxidation of the compounds of formulae (II) or (IIa) to give the compounds of formulae (I) or (Ia) is performed in the presence of an organic solvent or an organic solvent mixture.

If the oxidation reaction is carried out in the presence of an organic solvent, it is preferred that the organic solvent is inert under the reaction conditions. Preferred inert organic solvents are, by way of example, aliphatic or alicyclic hydrocarbons, in particular alkanes and cycloalkanes having 5 to 12 carbon atoms, halogenated aliphatic hydrocarbons, and aromatic and substituted aromatic hydrocarbons, aliphatic or alicyclic ethers and alkyl esters. Examples of inert solvents are aliphatic hydrocarbons, such as pentane, hexane, heptane, ligroin, petrol ether, cyclohexane, halogenated hydrocarbons, such as dichloromethane, trichloromethane, tetrachloromethane or dichloroethane, aromatics, such as benzene, toluene, xylenes, chlorobenzene, dichlorobenzenes, aliphatic or alicyclic ethers such as methyl-tert.-butylether, dibutyl ether, tetrahydrofurane, 1,4-dioxane, 1,2-dimethoxyethane, alkyl esters, such as ethyl acetate or propyl acetate, and mixtures thereof.

In a particularly preferred embodiment of the present invention, the oxidation of the compounds of formulae (II) or (IIa) to the compounds of formulae (I) or (Ia) is performed in the presence of an organic solvent or an organic solvent mixture selected from water immiscible, non-halogenated organic solvents.

Examples of particularly preferred inert organic solvents are aliphatic hydrocarbons, such as hexane, heptane, petrol ether or cyclohexane; aromatics, such as benzene, toluene or xylenes; ethers, such as methyl-tert.-butylether, dibutyl ether, tetrahydrofurane, 1,4-dioxane or 1,2-dimethoxyethane; alkyl esters, such as ethyl acetate or propyl acetate; and mixtures thereof. Especially preferred are methyl-tert.-butylether and ethyl acetate.

The process of the invention can be performed either continuously or batchwise. The batchwise oxidation can be conducted in a reaction apparatus conventionally used for this purpose, e.g. a stirred reactor, which is optionally equipped with metering devices. The process according to the present invention may also be carried out continuously, e.g. in a tube reactor or in a cascade of at least two stirred reactors, which may be back-mixed or not.

The reaction mixture can be subjected to conventional work-up including e.g. extractive aqueous work-up, removal of volatiles and the like.

In a preferred embodiment of the present invention, the ruthenium compound is recovered from the reaction mixture after completion of the oxidation of the compound of formula (II) or (IIa), respectively, for further use or reuse.

The recycling of the ruthenium compound can for example be achieved by simple filtration of the organic phase, followed by one or several washing steps with water and/or the organic solvent. After the washing steps, the ruthenium compound may be dried for one to several hours, e.g. 2 or 3 hours, at elevated temperature, for example at a temperature of 40, 50 or 60° C. The thus obtained ruthenium compound can directly be used for further oxidation reactions.

Alternatively, the ruthenium compound can also be reused directly after filtration without any washing and/or drying steps.

If a water immiscible organic solvent is used for the oxidation reaction and an alkaline aqueous solution of the co-oxidizing agent and/or an aqueous buffer solution are added to the reaction mixture, the reaction mixture typically consist of two phases. In this case, the work-up procedure can for example conveniently be performed as follows: After completion of the reaction, the two phases are separated and the residual water phase is washed several times with the organic solvent, whereupon removal of the ruthenium compound by filtration and evaporation of the organic solvent, the compounds of formulae (I) or (Ia), respectively, are obtained as an crude product.

The obtained crude product may be subjected to conventional purification measures, including distillation or chromatography or combined measures. Suitable distillation devices for the purification of the compounds of formulae (I) or (Ia), respectively, include, for example, distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof.

The starting compounds of the formulae (II) or (IIa) are known e.g. from DE 2916418; they are commercially available or they can be prepared by analogy to the methods described in DE 2916418.

EXAMPLES

I) Gas Chromatographic Analysis

GC-System and Separation Method:
GC-system: Agilent 5890 Series II;
GC-Column: 5CB-WAX-52CB (50 m (Length), 0.32 mm (ID), 1.2 μm (Film));
Temperature program: 40° C. for 6 minutes, 40° C. to until 250° C. in 8° C./min.

II) Production Examples

Example 1: Oxidation of IIa in 1,2-Dichloroethane 5.0 g (22.7 mmol) of the monoene of formula (IIa) and 0.3 g (1.15 mmol) $RuCl_3$ in 25 ml 1,2-dichloromethane were placed into a 250 ml reaction flask, equipped with an 100 ml dropping funnel, an intensive condenser and a mechanical stirrer. Under vigorous stirring at 35° C., 75 ml of a 12.5 weight-% NaOCl-solution (126 mmol) in $H_2O$ charged with 1.5 g NaOH, were added. The pH of the reaction mixture was 14.0 at the start of the addition and dropped to pH 7.9 over time.

The course of the oxidation reaction was followed by gas chromatographic analysis: After 2 hours, the conversion of the monoene (IIa) was 100% and the formation of the diketone of formula (Ia) 80% (GC area percent). After 3 hours, the formation of the diketone of formula (Ia) reached 94% (GC area percent).

After completion of the reaction, the reaction mixture was allowed to cool down to room temperature and the organic phase was separated from the water phase. The water phase was washed with 1,2-dichloromethane. The ruthenium compound (catalyst) was separated from the organic phase by filtration and washed with 1,2-dichloromethane and water. The combined organic phases were dried over sodium sulfate and the solvent was removed under reduced pressure. An analysis of the reaction residual revealed 100% conversion of the monoene (IIa) and the formation of the wanted diketone of formula (Ia) of 95% (GC weight percent).

Example 2: Oxidation of IIa in Ethyl Acetate and in the Presence of a Buffer Solution 5.0 g (22.7 mmol) of the monoene of formula (IIa), 0.3 g (1.15 mmol) $RuCl_3$ in 25 ml ethyl acetate and 25 ml of a $Na_2CO_3$/$NaHCO_3$ buffer solution (pH 9.7) were placed into a 250 ml reaction flask, equipped with an 100 ml dropping funnel, an intensive condenser and a mechanical stirrer. Under vigorous stirring at 35° C., 75 ml of a 12.5 weight-% NaOCl-solution (126 mmol) in $H_2O$ charged with 1.5 g NaOH, were added. The pH of the reaction mixture was 10.8 at the start of the addition and dropped to pH 9.0 over time.

The course of the oxidation reaction was followed by gas chromatographic analysis: After 2 hours, the conversion of the monoene (IIa) was 99.6% and the formation of the diketone of formula (Ia) 77.6% (GC area percent).

After completion of the reaction, the reaction mixture was allowed to cool down to room temperature and the organic phase was separated from the water phase. The water phase was washed with ethyl acetate. The ruthenium compound (catalyst) was separated from the organic phase by filtration and washed with ethyl acetate and water. The combined organic phases were dried over sodium sulfate and the solvent was removed under reduced pressure. An analysis of the reaction residual revealed 100% conversion of the monoene (IIa) and the formation of the wanted diketone of formula (Ia) of 83.5% (GC weight percent).

Example 3: Oxidation of IIa in Ethyl Acetate Without the Addition of a Buffer Solution 5.0 g (22.7 mmol) of the monoene of formula (IIa) and 0.3 g (1.15 mmol) $RuCl_3$ in 25 ml ethyl acetate were placed into a 250 ml reaction flask, equipped with an 100 ml dropping funnel, an intensive condenser and a mechanical stirrer. Under vigorous stirring at 35° C., 75 ml of a 12.5 weight-% NaOCl-solution (126 mmol) in $H_2O$ charged with 1.5 g NaOH, were added. The pH of the reaction mixture was 14.0 at the start of the addition and dropped to pH 7.6 over time.

The course of the oxidation reaction was followed by gas chromatographic analysis: After 2 hours, the conversion of the monoene (IIa) was 100% and the formation of the diketone of formula (Ia) 66.7% (GC area percent).

After completion of the reaction, the reaction mixture was allowed to cool down to room temperature and the organic phase was separated from the water phase. The water phase was washed with ethyl acetate. The ruthenium compound (catalyst) was separated from the organic phase by filtration and washed with ethyl acetate and water. The combined organic phases were dried over sodium sulfate and the solvent was removed under reduced pressure. An analysis of the reaction residual revealed 100% conversion of the monoene (IIa) and the formation of the wanted diketone of formula (Ia) of 75.8% (GC weight percent).

Example 4: Oxidation of IIa in Methyl Tert.-Butyl Ether (MTBE) and in the Presence of a Buffer Solution 5.0 g (22.7 mmol) of the monoene of formula (IIa), 0.3 g (1.15 mmol) $RuCl_3$ in 25 ml MTBE and 25 ml of a $Na_2CO_3/NaHCO_3$ buffer solution (pH 9.7) were placed into a 250 ml reaction flask, equipped with an 100 ml dropping funnel, an intensive condenser and a mechanical stirrer. Under vigorous stirring at 35° C., 75 ml of a 12.5 weight-% NaOCl-solution (126 mmol) in $H_2O$ charged with 1.5 g NaOH, were added. The pH of the reaction mixture was 12.7 over the course of the reaction. The course of the oxidation reaction was followed by gas chromatographic analysis. The total reaction time was 5 hours.

After completion of the reaction, the reaction mixture was allowed to cool down to room temperature and the organic phase was separated from the water phase. The water phase was washed with MTBE. The ruthenium compound (catalyst) was separated from the organic phase by filtration and washed with MTBE and water. The combined organic phases were dried over sodium sulfate and the solvent was removed under reduced pressure. An analysis of the reaction residual revealed 100% conversion of the monoene (IIa) and the formation of the wanted diketone of formula (Ia) of 66.3% (GC weight percent).

Example 5: Oxidation of IIa in Methyl Tert.-Butyl Ether (MTBE) Without the Addition of a Buffer Solution 5.0 g (22.7 mmol) of the monoene of formula (IIa) and 0.3 g (1.15 mmol) $RuCl_3$ in 25 ml MTBE were placed into a 250 ml reaction flask, equipped with an 100 ml dropping funnel, an intensive condenser and a mechanical stirrer. Under vigorous stirring at 35° C., 75 ml of a 12.5 weight-% NaOCl-solution (126 mmol) in $H_2O$ charged with 1.5 g NaOH, were added. The pH of the reaction mixture was 9.4 over the course of the reaction. The course of the oxidation reaction was followed by gas chromatographic analysis. The total reaction time was 5 hours.

After completion of the reaction, the reaction mixture was allowed to cool down to room temperature and the organic phase was separated from the water phase. The water phase was washed with MTBE. The ruthenium compound (catalyst) was separated from the organic phase by filtration and washed with MTBE and water. The combined organic phases were dried over sodium sulfate and the solvent was removed under reduced pressure. An analysis of the reaction residual revealed 100% conversion of the monoene (IIa) and the formation of the wanted diketone of formula (Ia) of 93.6% (GC weight percent).

Example 6: Large Batch Oxidation of IIa in Methyl Tert.-Butyl Ether (MTBE)

89.5 g (0.40 mol) of the monoene of formula (IIa) and 5.8 g (23 mmol) $RuCl_3$ in 500 ml MTBE were placed into a 2.5 l H=D reactor equipped with an 1 l dropping funnel, an intensive condenser and a 3-fold cross-arm stirrer (400 rpm). Under vigorous stirring at 35° C., 1.0 l of a 13.4 weight-% NaOCl-solution in $H_2O$ (1.80 mol), charged with 26.5 g NaOH (0.66 mol), were added. Following this, the reaction was run at 35° C. for additional 10 hours.

The course of the oxidation reaction was followed by gas chromatographic analysis: After 5 hours, the conversion of the monoene (IIa) was 83% and the formation of the diketone of formula (Ia) 72% (GC area percent). After 10 hours, the conversion of the monoene (IIa) was 100% and the formation of the diketone of formula (Ia) 91% (GC area percent).

After completion of the reaction, the reaction mixture was allowed to cool down to room temperature and the organic phase was separated from the water phase. The water phase was washed with MTBE. The organic phase was first washed with 250 ml of a 20 weight-% solution of NaOH in water followed by 250 ml of water. The ruthenium compound (catalyst) was separated from the organic phase by filtration and washed with MTBE and water. After this washing step, the ruthenium compound (catalyst) was dried at 50° C. for 2 hours and directly applied to the next oxidation reaction (vide example 7).

The combined organic phases were dried over sodium sulfate and the solvent was removed under reduced pressure. 120.8 g of residual were obtained. An analysis of the residual revealed complete conversion of the monoene (IIa) and 76.7% of the wanted diketone (92.6 g, 0.367 mol, 91.7% yield).

Example 7: Large Batch Oxidation of IIa in Methyl Tert.-Butyl Ether (MTBE) Using the Recovered Ruthenium Compound (Catalyst) of Example 6

89.5 g (0.40 mol) of the monoene of formula (IIa) and 5.9 g of recovered ruthenium compound (catalyst) from example 6 in 500 ml MTBE were placed into a 2.5 l H=D—reactor equipped with an 1 l dropping funnel, an intensive condenser and a 3-fold cross-arm stirrer (400 rpm). Under vigorous stirring at 35° C., 1.0 l of a 13.4 weight-% NaOCl-solution in $H_2O$ (1.80 mol), charged with 26.5 g NaOH (0.66 mol), were added. Following this, the reaction was run at 35° C. for additional 10 hours.

The course of the oxidation reaction was followed by gas chromatographic analysis: After 5 hours, the conversion of the monoene (IIa) was 85% and the formation of the diketone of formula (Ia) 74% (GC area percent). After 10 hours, the conversion of the monoene (IIa) was 100% and the formation of the diketone of formula (Ia) 89% (GC area percent).

After completion of the reaction, the reaction mixture was allowed to cool down to room temperature and the organic phase was separated from the water phase. The water phase was washed with MTBE. The organic phase was first washed with 250 ml of a 20 weight-% solution of NaOH in water followed by 250 ml of water. The ruthenium compound (catalyst) was separated from the organic phase by filtration and washed with MTBE and water. After this washing step, the ruthenium compound (catalyst) was dried at 50° C. for 2 hours.

The combined organic phases were dried over sodium sulfate and the solvent was removed under reduced pressure. 102.3 g of residual were obtained. An analysis of the residual revealed complete conversion of the monoene (IIa) and 89% of the wanted diketone (91.0 g, 0.361 mol, 90.3% yield).

The invention claimed is:
1. A process for preparing a macrocyclic diketone compound of the formula (I), which comprises the oxidation of a bicycloolefine compound of the formula (II) with an oxidizing agent,

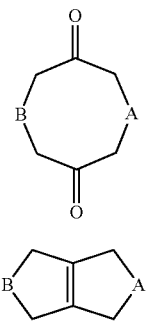

where in formulae (I) and (II)

A is $(CH_2)_n$ with n being an integer from 2 to 12, where two hydrogen atoms are optionally replaced by $C_1$-$C_4$-alkyl or two hydrogen atoms, which are bound to adjacent carbon atoms are optionally replaced by a fused 5- or 6-membered saturated carbocycle;

B is $(CH_2)_m$ with m being 1 or 2, where 1 or 2 hydrogen atoms are optionally replaced by $C_1$-$C_4$-alkyl, where the oxidizing agent comprises a catalytic amount of a ruthenium compound and a co-oxidizing agent selected from oxyanions of chlorine.

2. The process of claim 1, where the total amount of the ruthenium compound in the reaction mixture, calculated based on the number of ruthenium atoms, is in the range of from 0.001 to 0.2 mol per 1 mol of compound of formula (II).

3. The process of claim 1, where the ruthenium compound is selected from the group consisting of ruthenium oxides, ruthenates, perruthenates, ruthenium halides, ruthenium nitrates and mixtures thereof.

4. The process of claim 1, where the total amount of the co-oxidizing agent used in the oxidation is in the range of from 2 to 10 mol per 1 mol of compound of formula (II), calculated as oxygen equivalent.

5. The process of claim 1, where the co-oxidizing agent is selected from hypochlorites.

6. The process of claim 1, where the pH of the reaction mixture is maintained in the range of from 7 to 14 during the oxidation of the compound of formula (II).

7. The process of claim 6, where the maintenance of the pH is achieved by adding an aqueous buffer solution, comprising at least one buffering agent, having a pKa-value in the range of from 8 to 12, to the reaction mixture.

8. The process of claim 1, where the co-oxidizing agent is added to the reaction mixture in the form of an alkaline aqueous solution, having a pH of at least pH 10.

9. The process of claim 1, where the co-oxidizing agent is added continuously to the reaction mixture during the oxidation of the compound of formula (II).

10. The process of claim 1, where the molar ratio of the co-oxidizing agent to the ruthenium compound, which are applied to the reaction mixture, is in the range of from 10:1 to 10000:1.

11. The process of claim 1, where the oxidation of the compound of formula (II) is performed in the presence of an organic solvent or an organic solvent mixture.

12. The process of claim 1, where, after completion of the oxidation of the compound of formula (II), the ruthenium compound is recovered from the reaction mixture for further reuse.

13. The process of claim 1, where the compound of formula (I) is 3-methylcyclopentadecane-1,5-dione and the compound of formula (II) is 14-methylbicyclo[10.3.0]pentadecen[1(12)].

14. The process of claim 1, where the compound of formula (I) is cyclopentadecane-1,5-dione and the compound of formula (II) is bicyclo[10.3.0]pentadecen[1(12)].

* * * * *